United States Patent
Fellows

(10) Patent No.: US 10,933,026 B2
(45) Date of Patent: *Mar. 2, 2021

(54) METHOD FOR MANUFACTURING A THERAPEUTIC AGENT FOR USE IN THE TREATMENT OF INFECTIONS

(71) Applicant: AGA NANOTECH LTD, London (GB)

(72) Inventor: Adrian Neville Fellows, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/874,552

(22) Filed: Jan. 18, 2018

(65) Prior Publication Data
US 2018/0207105 A1 Jul. 26, 2018

Related U.S. Application Data

(63) Continuation of application No. 15/126,511, filed as application No. PCT/GB2015/000100 on Mar. 24, 2015, now Pat. No. 9,913,805.

(30) Foreign Application Priority Data

Apr. 1, 2014 (GB) .................................. 1405874
Aug. 26, 2014 (GB) .................................. 1415063

(51) Int. Cl.
| | | |
|---|---|---|
| A61K 9/51 | (2006.01) | |
| A61K 9/50 | (2006.01) | |
| A61K 31/327 | (2006.01) | |
| A61K 33/40 | (2006.01) | |
| A61K 31/16 | (2006.01) | |
| A61K 9/107 | (2006.01) | |
| A61K 45/06 | (2006.01) | |

(52) U.S. Cl.
CPC .......... *A61K 9/5153* (2013.01); *A61K 9/1075* (2013.01); *A61K 9/5031* (2013.01); *A61K 31/16* (2013.01); *A61K 31/327* (2013.01); *A61K 33/40* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 9,913,805 | B2 * | 3/2018 | Fellows ................. | A61K 45/06 |
| 2010/0196503 | A1 * | 8/2010 | Heisig .................... | A61K 31/16 |
| | | | | 424/616 |

(Continued)

FOREIGN PATENT DOCUMENTS

WO WO-2005112631 A2 * 12/2005 ............. A01N 25/34

OTHER PUBLICATIONS

Nisco. www.nisco.ch/var_d_classic.htm accessed Nov. 18, 2020, 2 printed pages. (Year: 2020).*

*Primary Examiner* — Isaac Shomer

(57) ABSTRACT

A method of manufacturing a therapeutic agent for the treatment of infections includes the steps of preparing a homogeneous solution of poly(DL-lactide-co-glycolide acid), preparing a solution of a peroxygen donor, preparing a solution of an acetyl donor, adding each of the solutions to a quantity of the poly(DL-lactide-co-glycolide acid) solution to produce a resultant mixture, preparing encapsulated nano- or micro-scale particles from the resultant mixture using a microencapsulator, collecting the nano- or micro-scale particles, and subsequently subjecting the particles to a lyophilization process.

24 Claims, 3 Drawing Sheets

(56) References Cited

U.S. PATENT DOCUMENTS

2010/0247663 A1* 9/2010 Day ................. A61K 9/19
　　　　　　　　　　　　　　　　424/497
2011/0218140 A1* 9/2011 Gonsalves ........... A61K 9/5138
　　　　　　　　　　　　　　　　514/2.9

* cited by examiner

METHOD FOR MANUFACTURING A THERAPEUTIC AGENT FOR USE IN THE TREATMENT OF INFECTIONS

CROSS-REFERENCE TO RELATED APPLICATIONS

The present application is a continuation of U.S. application Ser. No. 15/126,511, filed on Sep. 15, 2016, and entitled "A Therapeutic Agent for Use in the Treatment of Infections", presently pending.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to a micro- or nano-scale therapeutic agent for use in the treatment of infections of humans or animals. Such an infection may be a systemic or a topical infection.

2. Description of Related Art Including Information Disclosed Under 37 CFR 1.97 and 37 CFR 1.98

Antibiotic resistance, particularly the emergence of widespread multiple drug resistant infections, poses a catastrophic risk to human health and involves substantial costs. Novel approaches to combat infection are therefore urgently required.

It is an object of the present invention to provide a therapeutic agent for use in the treatment of infections of humans and animals, including multiple drug resistant infections, in a wide range of infection sites and physiological environments.

It is a further object to provide a therapeutic agent that at least in some embodiments will minimize the likelihood of resistance in the target infecting organism.

These and other objects and advantages of the present invention will become apparent from a reading of the attached specification and appended claims.

BRIEF SUMMARY OF THE INVENTION

According to the present invention there is provided a nano- or micro-scale therapeutic agent comprising micro- and/or nano-particle carriers loaded singly or in combination with one or more inert precursor chemical or chemicals, the carriers encapsulating the precursor chemical or chemicals which after release from the carrier in situ at the site of an infection are activatable by the physiological milieu to form an antimicrobial agent for use in the treatment of said infection of a human or animal.

Preferably, the precursor chemical or chemicals form an oxidative biocide on activation.

Highly oxidative molecules exert a powerful biocidal effect on micro-organisms by inflicting massive and widely disseminated damage to the bacterial cell owing to the high energy transfer capability of these molecules. Therefore resistance to these chemicals is rare. Examples of such molecules would be ozone, hypochlorous acid, sodium hypochlorite or hypobromite, chlorine dioxide, peracids such as peracetic acid and hydrogen peroxide. It is not generally practical to use these powerful chemicals for therapeutic purposes but when the encapsulated precursor chemical or chemicals are delivered in micro- and/or nano-particles directly to the target infecting organism production of these chemicals does not occur until the precursor chemical or chemicals are activated in situ at the site of an infection, for example by contact with body fluids.

In particular, the precursor chemical or chemicals preferably comprise one or more peroxygen donors that on release are activated to form hydrogen peroxide.

Preferably also, release of the precursor chemical or chemicals occurs when the carrier bursts, degrades or changes its porosity in situ, which may be within or, in the case of a topical use, on the body of the human or animal host. Advantageously, the carrier degrades via hydrolysis over time to provide a controlled release of the precursor chemical or chemicals.

Examples of suitable micro- and/or nano-particle carriers for use in the present invention are micelles, dendrimers, buckyballs, liposomes, ethosomes, mesoporous silica and nano-carbon tubes, all of which are capable of encapsulating other chemicals. Advantageously but not necessarily, the carrier is in the form of micro- and/or nano-particles that have been manufactured using a thermally induced phase separation (TIPS) process. Such a process minimises residues of solvents used in the encapsulation process that may otherwise compromise the safety and efficacy of the resulting therapeutic agent. In addition, in some cases it is preferable for the carrier to be biodegradable within the body of the host to produce harmless by-products, Preferably, therefore, the carrier is comprised of a biodegradable polymer such as poly(lactic-co-glycolic acid) (PLGA) that can be used to produce micro- and/or nano-particles encapsulating the precursor chemicals by a TIPS process.

PLGA is a copolymer that is synthesized by means of ring-opening co-polymerization of two different monomers, the cyclic dimers (1,4-dioxane-2,5-diones) of glycolic acid and lactic acid. It undergoes hydrolysis in vivo to produce the original monomers, lactic acid and glycolic acid, which under normal physiological conditions are by-products of various metabolic pathways in the body. Hence, there is minimal systemic toxicity associated with using PLGA for the purpose of the present invention.

Examples of the production of therapeutic agents of this type and in accordance with the invention are described below.

Advantageously, the precursor chemicals also comprise one or more acetyl donors that on release react with the hydrogen peroxide produced by the peroxygen donor to produce a mixture of peracetic acid and hydrogen peroxide. The acetyl donor or donors may be encapsulated within the same carrier particles as the peroxygen donor. Preferably, therefore, the therapeutic agent of the invention comprises micro- and/or nano-particle carriers wherein at least a proportion of them each encapsulate both a peroxygen donor and an acetyl donor. Alternatively or in addition, the acetyl donor is encapsulated within its own micro- and/or nano-particle carriers and the therapeutic agent of the invention comprises a combination of micro- and/or nano-particle carriers that individually encapsulate either the peroxygen donor or donors or the acetyl donor or donors.

Hydrogen peroxide is widely used in endodontics, in the treatment of periodontitis and as an antiseptic for wounds and mucous membranes. Dilute solutions of hypochlorous acid have been advocated for topical disinfection and per-acetic acid has been widely used in dairy hygiene as a pre- and post-milking teat disinfectant. However delivering these highly active agents to the site of more serious deep-seated infections in a controlled, safe and effective manner is largely impractical using conventional methods. The present invention overcomes this problem by encapsulating the precursor chemicals in a carrier whereby the antimicrobial agent is only created after the carrier has reached the target and released the precursor chemicals, which are then activated on contact with the target by the physiological milieu, for example by contact with body fluids.

The use of an inert precursor chemical that can be activated in situ overcomes problems of stability and safety for the active antimicrobial agent. In the present invention preferably a combination of a peroxygen donor with an acetyl donor is used to produce dynamic equilibrium mixtures of hydrogen peroxide and peracetic acid.

The peroxygen donor preferably comprises any or a combination of the chemicals in the following List A.

| List A |
|---|
| Sodium perborate |
| Sodium percarbonate |
| Sodium perphosphate |
| Urea peroxide |
| Peresters |
| Superoxides |
| Dioxygenyl |
| Ozones |
| Hydrogen peroxide |
| Lithium peroxide |
| Barium peroxide |
| Di-tert-butyl peroxide |
| Ammonium peroxydisulphate |
| Potassium peroxymonosulphate |

Any or a combination of sodium percarbonate, potassium percarbonate, ammonium percarbonate, sodium perborate, ammonium perborate, ammonium persulphate and urea peroxide from List A are particularly preferred.

There are many acetyl donors which react with hydrogen peroxide released from the peroxygen donor on the addition of water. The acetyl donor preferably comprises any or a combination of the chemicals in the following List B.

| List B |
|---|
| Tetraacetylethylenediamine (TAED) |
| Methyl cellulose encapsulated TAED or encapsulated donors |
| Acetyl salicylic acid |
| Diacetyl dioxohexahydratriazine (DADHT) |
| Tetraacetyl glycoluril |
| Acetyl urea |
| Di-acetyl urea |
| Tri-acetyl urea |
| Pentaacetyl glucose (PAG) |
| Tetraacetyl glycoluril (TAGU) |
| Acetyl phosphate |

| List B -continued |
|---|
| Acetyl imidazole |
| Acetyl CoA |
| Acetic anhydride |
| Compounds containing a hemiacetal group |
| Acetic acid |
| Di-, acetylmorphine |
| Pyruvate |
| Acetyl chloride |
| Acetyl-caprolactam |
| N'N'-Diacetyl-N'N'-dimethyl urea. |

The use of tetraacetylethylenediamine (TAED) as the acetyl donor is especially preferred.

The choice of the peroxygen and acetyl donors is dependent on the physiological milieu to be encountered during use of the therapeutic agent. Those that degrade to produce substances that are either naturally occurring or well tolerated within the body being preferred for in vivo use but others may be appropriate for use externally, for example in the topical treatment of skin infections or for use within a void, fissure or lumen.

As indicated above, the carrier may comprise micro-particles, nano-particles or a mixture of the two. In accordance with the IUPAC (International Union of Pure and Applied Chemistry) definitions, micro-particles are particles of any shape with dimensions in the $1\times10^{-7}$ m and $1\times10^{-4}$ m range whereas nano-particles are particles of any shape with dimensions in the $1\times10^{-9}$ m to $1\times10^{-7}$ m range. Particle size and size distribution are the most important characteristics of micro- and nano-particle systems. They determine the in vivo distribution, biological fate, toxicity and the targeting ability of the carrier. In addition, they can also influence the drug loading, drug release and stability of the carrier. Nano-particles of sub-micron size have a number of advantages over micro-particles as drug carriers as they have a relatively higher intracellular uptake compared to micro-particles and are available to a wider range of biological targets owing to their small size and relative mobility. However, in specific situations, for example when packing of the particles within a void, fissure or lumen may be beneficial, micro-particles may be selected and prove more advantageous for use than nano-particles.

Poly(lactic-co-glycolic acid) (PLGA)—based particles can be produced over a size range from around $20\times10^{-3}$ μm diameter up to micron sizes. The production of such particles is known and described, for example, in WO2008/155558. The method of manufacture of these particles can be used to manipulate their properties such as porosity, payload efficiency and drug release profile. This makes them particularly suited to being the carrier in this invention. Loading of these particles with the precursor chemical can be achieved by known techniques either during the particle fabrication process or afterwards.

Examples of methods of producing therapeutic agents in accordance with the present invention will now be described with reference to the accompanying drawings.

DETAILED DESCRIPTION OF THE INVENTION

In one method of manufacture therapeutic agents in accordance with the present invention are produced from PLGA solutions containing the active precursor chemicals by a thermally induced phase separation (TIPS) process. However, persons skilled in the art will be aware that other methods of manufacture are possible.

The TIPS process begins with production of a PLGA solution at a high temperature in order to generate a homogenous solution. The precursor chemical is dissolved in a suitable solvent and is then blended into the PLGA solution. The removal of thermal energy by rapid cooling below a biomodal solubility curve using another immiscible cooling liquid induces the phase de-mixing of the homogenous PLGA solution into a multi-phase system containing a PLGA-rich phase and PLGA-lean phase. The phase separated PLGA solution is subsequently treated by freeze-drying to remove the solvents, generating the micro- and/or nano-particles of the invention.

In particular to produce a sample of micro- and nano-particles that encapsulate sodium percarbonate, poly(DL-lactide-co-glycolide), for example that sold under the registered trade mark PURASORB® PDLG IV 0.68 dl/g by Corbion Group Netherlands BV, was dissolved in dimethyl carbonate to produce a 4 wt % solution under magnetic stirring 24 hr before use. The sodium percarbonate was dissolved in ultrapure water at 100 mg/ml by vortexing and then by being allowed to stand for 24 hours. Thereafter, 833 μl of the sodium percarbonate solution was added to 7.5 ml of the PLGA solution in a capped 10 ml glass vial before mixing by vortexing.

TIPS micro- and nano-particles were then prepared using a conventional microencapsulator, for example an Encapsulator VAR-D unit as manufactured by Nisco Engineering AG. The particles produced were collected in liquid nitrogen before being transferred to a freeze-drier for lyophilisation. The resulting particles are as shown in FIGS. 1 and 2.

A similar method was also used to produce micro- and nano-particles that encapsulate urea hydrogen peroxide except that urea hydrogen peroxide was used in place of the sodium percarbonate and was dissolved in methanol at 100 mg/ml. The resulting particles are as shown in FIGS. 3 and 4.

The aforesaid methods produced micro- and nano-particles with a loading concentration of 278 mg of the relevant precursor chemical per g PLGA. It is expected that higher concentrations up to approximately double this amount are also achievable if necessary.

Figure 1:
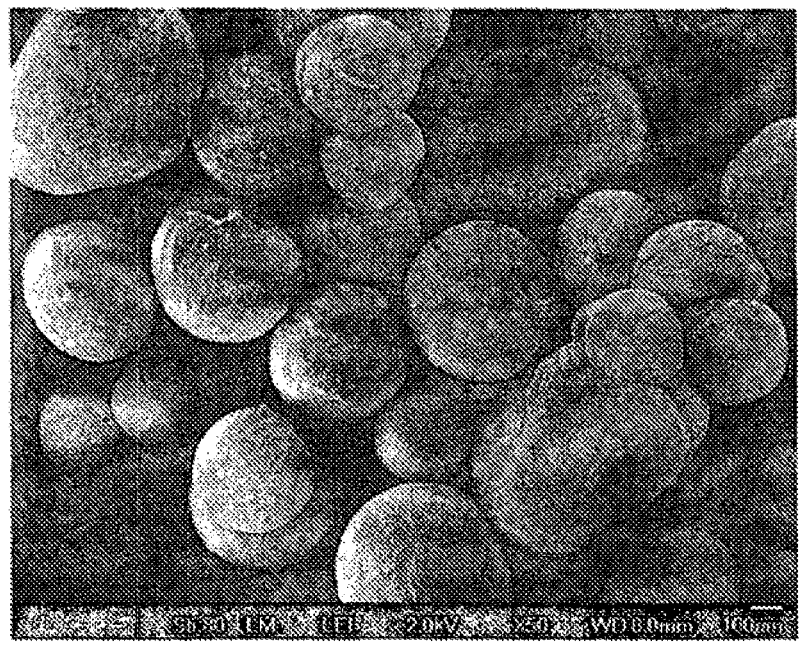
FIG. 1 is a is photograph of an image produced by a scanning electron microscope of PLGA micro- and nano-particles encapsulating sodium percarbonate.
Figure 2:
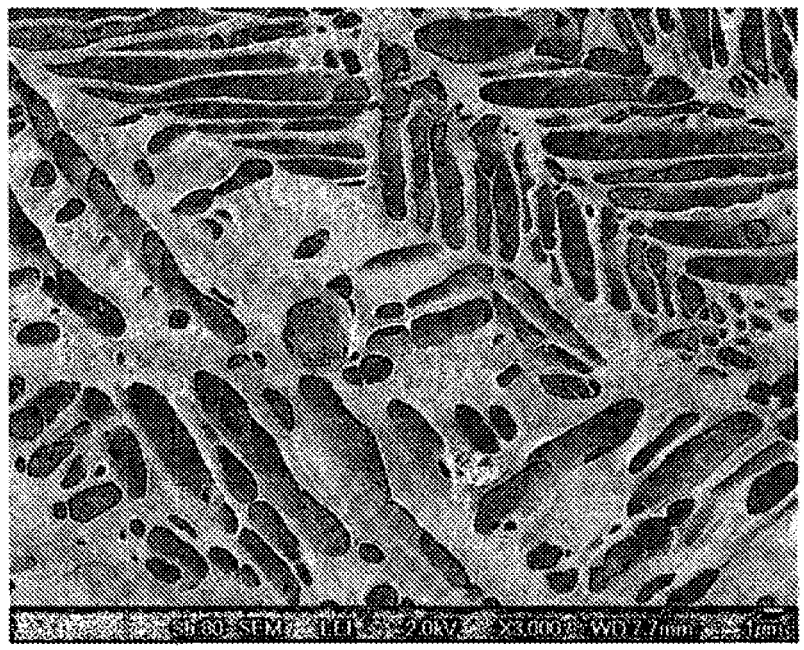
FIG. 2 is photograph of an image produced by a scanning electron microscope of one of the micro-particles shown in FIG. 1 but to a greater magnification.
Figure 3:
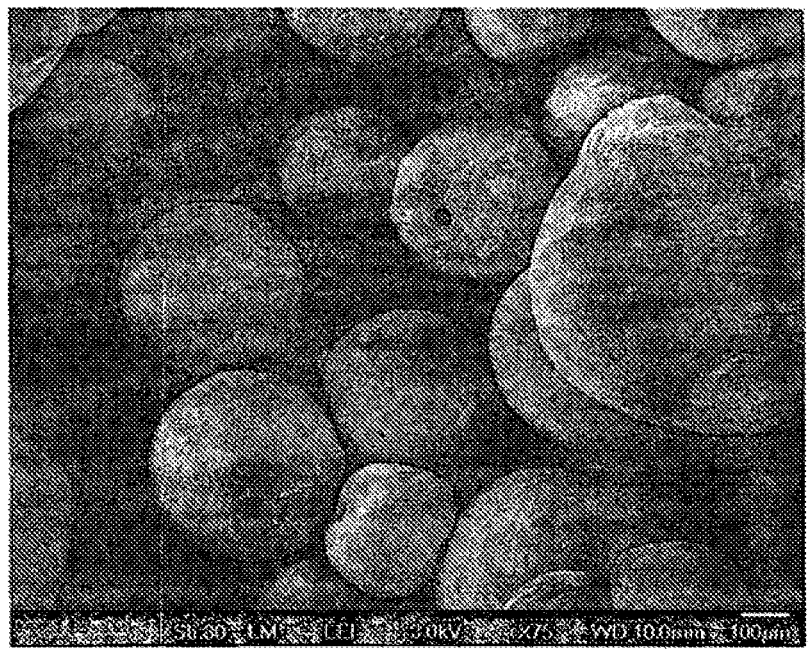
FIG. 3 is photograph of an image produced by a scanning electron microscope of PLGA micro- and nano-particles encapsulating urea hydrogen peroxide.
Figure 4:
FIG. 4 is photograph of an image produced by a scanning electron microscope of one of the micro-particles shown in FIG. 3 but to a greater magnification.

As shown in FIGS. 1 and 3, the micro- and nano-particles produced have a rugose and porous surface typical of TIPS particles. The surface of both sets of particles show deposits of amorphous material that is most likely to comprise the loaded precursor chemical active ingredient. A large pore was also visible on the surface of many of the micro-particles, which is also a characteristic feature of TIPS micro- and nano-particles. The precursor chemical is also encapsulated by the PLGA carrier, which is contained within the particles in a dry form, the solvents having been removed by the freeze-drying. It is desirable that the solvents used in the manufacturing process are removed or only minimally present as they can increase the toxicity of the particles. Also, if the precursor chemicals were encapsulated in solution their stability over time would be compromised. The TIPS preparation method tends to minimise and even eliminate solvent residues and also has the advantage of giving a greater control over porosity of the micro- and nano-particles, which also determines the controlled release time of the precursor chemical from the particle. Micro- and nano-particles encapsulating a TAED acetyl donor using acetonitrile as a solvent for the TAED may also be prepared by a similar TIPS process.

Release of the precursor chemical from the micro- and nano-particles was also investigated to simulate its potential efficacy when in use in the treatment of infections of humans or animals.

Figure 5:
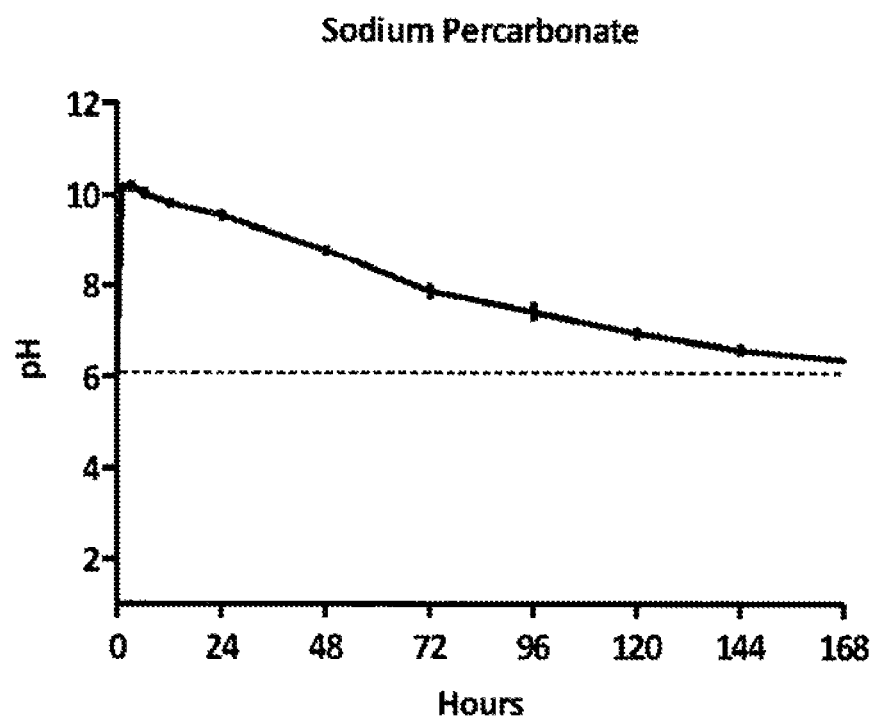
FIG. 5 is a graph showing the mean pH over time of samples of ultrapure water containing a concentration of 20 mg of the particles shown in FIGS. 1 and 2 per 1 ml water at 23° C.
Figure 6:
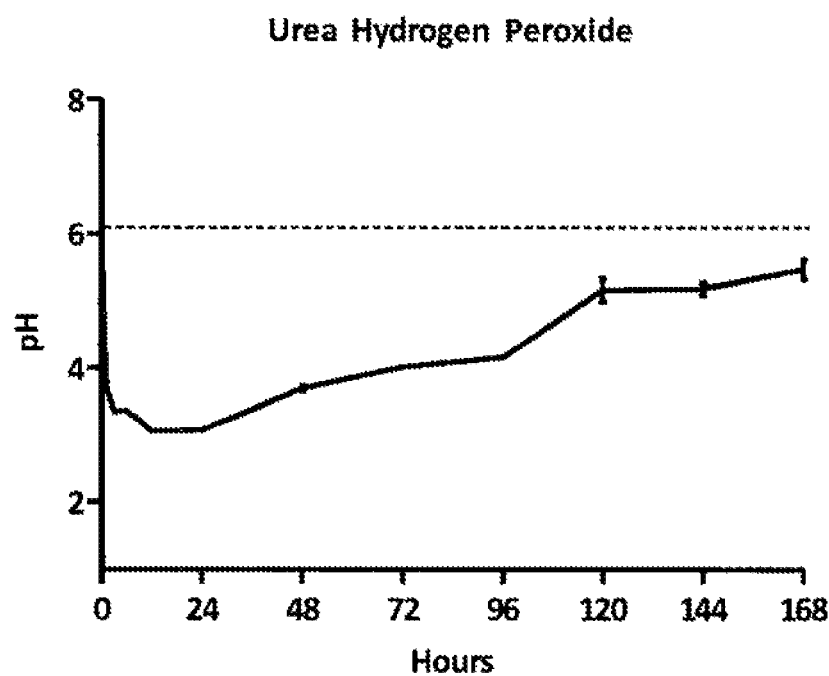
FIG. 6 is a graph showing the mean pH over time of samples of ultrapure water containing a concentration of 20 mg of the particles shown in FIGS. 3 and 4 per 1 ml water at 23° C.

The particles encapsulating sodium percarbonate and urea hydrogen peroxide described above were both used to test their capability in producing a change in pH of ultrapure water with an initial pH of 6.01 over a seven day test period. Samples of the particles were each placed into 2 ml polypropylene screw-cap microtubes and the ultrapure water was added to produce a final concentration of 20 mg micro- and nano-particles per 1 ml water. The particles were mixed by vortexing for 10 seconds before being incubated at 23° C. The pH of the samples was measured at pre-determined intervals. Each measurement was recorded after a pH electrode had been inserted into the sample for 2 minutes. The results are shown in FIGS. 5 and 6, the measurements being derived from four replicate samples with mean data being plotted showing standard error of mean.

It can be seen that the increase in pH produced by sodium percarbonate and the drop in pH produced by urea hydrogen peroxide was sustained throughout the incubation period despite the water immersing the particles being changed at 24 hour intervals. The change in pH values produced by the particles corresponds with the pH values of solutions of the active ingredients alone when dissolved in ultrapure water, as shown in the following Table 1.

TABLE 1

|  | 280 mg/ml | 140 mg/ml | 70 mg/ml | 35 mg/ml | 17.5 mg/ml |
| --- | --- | --- | --- | --- | --- |
| wt % | 28% | 14% | 7% | 3.5% | 1.75% |
| Sodium Percarbonate | 10.74 | 10.83 | 10.87 | 10.89 | 10.83 |
| Urea Hydrogen Peroxide | 4.97 | 6.38 | 6.9 | 6.92 | 7.90 |

It will be appreciated that the change in pH observed following incubation of the particles indicates that the precursor chemicals are capable of sustained release from the particles to produce a therapeutic agent in accordance with the invention over a prolonged period as the particles degrade. The release occurs as the encapsulating polymer degrades, which in the case of a PLGA polymer is via hydrolysis. It is expect that the release kinetics (rate and duration) can be modified by adjusting the composition of the polymer used to manufacture the micro- and nano-particles. Hence, the invention is not limited to the use of poly(lactic-co-glycolic acid) (PLGA)—based micro- and nano-particles. Micro- and nano-particles using a variety of synthetic and natural polymers may be utilised. Examples of such polymers are poly(allylamine)hydrochloride, poly(d-iallylmethylammonium chloride), polyethylenimine (PEI), polyvinyl pyrollidone, poly L ornithine, poly L arginine, protamines, chitosan, alginates, polystyrene sulphonate, poly(acrylic acid), poly(methacrylic acid), polyvinylsulfonate, poly phosphoric acid, poly L glutamic acid, alginates, and dextran sulphate. Nanomicellular carriers may also be made, for example, from polyethylene oxide/polypropylene oxide diblock and triblock copolymers, phospholipid or other surface active agents. Such carriers may be used in place or in addition to other micro- or nano-particle carriers.

The carriers may also be treated with secondary processes such as treatment with polyethylene glycol, usually styled PEGylation, to protect the particle in the physiological milieu and, for example, to give extended circulation time in the bloodstream. Alternatively or in addition the carriers may be treated with targeting ligands in order to provide enhanced target specificity. For example, the carriers may be targeted by a biosensor such as a monoclonal antibody.

Several other examples of the therapeutic agent of present invention are as follows.

1. Poly(lactic-co-glycolic acid) (PLGA)—based nano-particle carriers having a diameter of $200 \times 10^{-3}$ µm loaded with 10% of sodium percarbonate.

2. Poly(lactic-co-glycolic acid) (PLGA)—based nano-particle carriers having diameters in a range between $20 \times 10^{-3}$ µm and $100 \times 10^{-3}$ µm inclusive loaded with sodium percarbonate to a loading efficiency of 80%.

3. Poly(lactic-co-glycolic acid) (PLGA)—based nano-particle carriers loaded singly or in combination with sodium percarbonate and tetra acetyl ethylene diamine to a loading efficiency between 0.1% and 50%.

4. Polyethylenimine (PEI) carriers loaded singly or in combination with sodium persulphate and acetylsalicylic acid to a combined loading efficiency of 65%.

5. Poly(lactic-co-glycolic acid) (PLGA)—based nano-particle carriers having diameters in a range between 100 µm and 1000 µm inclusive loaded with urea peroxide to a loading efficiency of 75%.

6. PEGylated nano-particle carriers loaded with sodium percarbonate, the particles having diameters in a range between $20 \times 10^{-3}$ µm and $300 \times 10^{-3}$ µm inclusive with a loading efficiency of 40%.

7. Poly(lactic-co-glycolic acid) (PLGA)—based micro-particle carriers having a diameter of approximately 300 µm loaded with sodium percarbonate to a loading efficiency between 50% and 80% inclusive.

8. Chitosan-based nano-particles loaded with sodium percarbonate in admixture with PLGA particles loaded with tetra acetyl ethylene diamine, where the ratio of percarbonate to TAED is approximately 2:1.

The invention therefore combines well researched and widely used high level environmental antimicrobial agents and their biologically inert precursors encapsulated within a targeted micro- or nano-scale carrier. The precursor chemical or chemicals are sheltered from the immune responses of the host and prevented from causing unacceptable damage or side effect to the host tissues. Hence, the invention provides a therapeutically safe and effective means of targeting and killing infecting microorganisms, including multiple drug resistant organisms, and is capable of targeting a variety of body sites, including the bloodstream, the lungs, the liver, the kidneys, the gut, the urinary tract and the dermal layers.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. A method of manufacturing a therapeutic agent in the form of nano- or micro-scale particles for the treatment of an infection of a human or animal, the method comprising:
    preparing a homogeneous solution of poly(DL-lactide-co-glycolide acid) dissolved in acetonitrile or dimethyl carbonate;
    adding a peroxygen donor and an acetyl donor to a quantity of the poly(DL-lactide-co-glycolide acid) solution to produce a resultant mixture:
    preparing encapsulated nano- or micro-scale particles from said resultant mixture using a microencapsulator; and
    collecting the nano- or micro-scale particles and subsequently subjecting said particles to a lyophilization process.

2. The method of claim 1, the step of preparing a homogenous solution comprising:
    dissolving the poly(DL-lactide-co-glycolide acid) in the dimethyl carbonate to produce a 4 wt % solution.

3. The method of claim 1, wherein the peroxygen donor is sodium percarbonate.

4. The method of claim 3, further comprising:
    dissolving the sodium percarbonate in ultrapure water.

5. The method of claim 4, the step of dissolving comprising:
    dissolving the sodium percarbonate in ultrapure water at 100 mg/ml.

6. The method of claim 3, wherein the nano- or micro-scale particles have a diameter of $200 \times 10^{-3}$ µm and are loaded with 10% of sodium percarbonate.

7. The method of claim 3, wherein the nano- or micro-scale particles have diameters in a range of between $20 \times 10^{-3}$ µm and $100 \times 10^{-3}$ µm inclusive and are loaded with sodium percarbonate to a loading efficiency of 80%.

8. The method of claim 3, wherein the nano- or micro-scale particles have a diameter of approximately 300 µm and are loaded with sodium percarbonate to a loading efficiency of between 50% and 80% inclusive.

9. The method of claim 1, wherein the peroxygen donor is urea hydrogen peroxide.

10. The method of claim 9, further comprising:
    dissolving the urea hydrogen peroxide in methanol.

11. The method of claim 10, the step of dissolving comprising:
    dissolving the urea hydrogen peroxide in methanol at 100 mg/ml.

12. The method of claim 10, wherein the nano- or micro-scale particles have diameters in a range between 100 µm and 1000 µm inclusive and are loaded with the urea hydrogen peroxide to a loading efficiency of 75%.

13. The method of claim 1, wherein the acetyl donor is tetraacetylethylenediamine (TAED).

14. The method of claim 13, further comprising:
dissolving the tetraacetylethylenediamine (TAED) in acetonitrile.

15. The method of claim 3, wherein the acetyl donor is tetraacetylethylenediamine (TAED) and the nano- or micro-scale particles are loaded in combination with sodium percarbonate and tetra acetyl ethylene diamine to a loading efficiency between 0.1% and 50%.

16. The method of claim 1, further comprising:
mixing the peroxygen donor and of the acetyl donor with the poly(DL-lactide-co-glycolide) solution by vortexing.

17. The method of claim 1, further comprising:
collecting the nano- or micro-scale particles from the microencapsulator in liquid nitrogen.

18. The method of claim 1, further comprising:
PEGylating the nano- or micro-scale particles.

19. The method of claim 18, the step of PEGylating comprising:
PEGylating the nano- or micro-scale particles by treatment with polyethylene glycol.

20. The method of claim 18, wherein the peroxygen donor is sodium percarbonate and the PEGylated nano- or micro-scale particles have diameters in a range between $20 \times 10^{-3}$ µm and $300 \times 10^{-3}$ µm inclusive with a loading efficiency of 40%.

21. The method of claim 1, further comprising:
treating the nano- or micro-scale particles with a targeting ligand.

22. The method of claim 20, further comprising:
targeting the nano- or micro-scale particles with a biosensor.

23. The method of claim 21, wherein the biosensor is a monoclonal antibody.

24. The method of treating an infection in a human or an animal by the administration of a micro- and/or nano-scale therapeutic agent prepared by the method of claim 1.

* * * * *